US009463003B2

(12) United States Patent
Gordin et al.

(10) Patent No.: US 9,463,003 B2
(45) Date of Patent: Oct. 11, 2016

(54) MULTI-COMPONENTS DEVICE, SYSTEM AND METHOD FOR ASSISTING MINIMALLY INVASIVE PROCEDURES

(75) Inventors: Udi Gordin, Yuvalim (IL); Gilad Heftman, Kibutz Ein Gev (IL); Moran Sobol, Kibutz Gesher (IL)

(73) Assignee: Virtual Ports Ltd., Caesarea (IL)

( * ) Notice: Subject to any disclaimer, the term of this patent is extended or adjusted under 35 U.S.C. 154(b) by 679 days.

(21) Appl. No.: 12/995,825

(22) PCT Filed: Jun. 2, 2009

(86) PCT No.: PCT/IL2009/000550
§ 371 (c)(1),
(2), (4) Date: Dec. 2, 2010

(87) PCT Pub. No.: WO2009/147669
PCT Pub. Date: Dec. 10, 2009

(65) Prior Publication Data
US 2011/0124962 A1  May 26, 2011

Related U.S. Application Data

(60) Provisional application No. 61/058,229, filed on Jun. 3, 2008.

(51) Int. Cl.
*A61B 1/00* (2006.01)
*A61B 17/00* (2006.01)
*A61B 17/29* (2006.01)

(52) U.S. Cl.
CPC ......... *A61B 17/00234* (2013.01); *A61B 17/29* (2013.01); *A61B 2017/00283* (2013.01);
(Continued)

(58) Field of Classification Search
CPC .......... A61B 17/0206; A61B 17/0218; A61B 17/083
USPC ....... 600/201, 204, 206, 210, 215, 217, 218, 600/219; 606/151–153, 155–158
See application file for complete search history.

(56) References Cited

U.S. PATENT DOCUMENTS 1,648,228 A * 11/1927 Heidt .................. F16N 11/02
                                                          184/38.1
2,702,540 A *  2/1955 Debeh ............... A61B 17/0231
                                                          600/218
(Continued)

FOREIGN PATENT DOCUMENTS

EP         1648228        7/2004
WO    03/013366 A2       2/2003
(Continued)

OTHER PUBLICATIONS

Restriction Requirement mailed on Jul. 27, 2011 for U.S. Appl. No. 12/418,094, filed Apr. 3, 2009.
(Continued)

*Primary Examiner* — Ellen C Hammond
*Assistant Examiner* — Stuart S Bray
(74) *Attorney, Agent, or Firm* — Dekel Patent Ltd.; David Klein

(57) ABSTRACT

An elastic connector (ES) having at least two ends, each of which includes attachment means for reversibly attaching said ES to at least two components; wherein said ES is characterized by a predetermined default configuration: and, a queue-like configuration in which said ES is adapted to provide simultaneous queue-like insertion or extraction of said at least two components through a tube or endoscope's working channel or a trocar into or from a body cavity; said ES is adapted to be reversibly transformed from said predetermined default configuration to said queue-like configuration and from said queue-like configuration to said predetermined default configuration.

8 Claims, 12 Drawing Sheets

(52) U.S. Cl.
CPC ........... *A61B2017/00464* (2013.01); *A61B 2017/00477* (2013.01); *A61B 2017/00867* (2013.01); *A61B 2017/00876* (2013.01); *A61B 2017/294* (2013.01); *A61B 2017/2931* (2013.01)

(56) References Cited

U.S. PATENT DOCUMENTS

| | | | | |
|---|---|---|---|---|
| 3,182,373 A * | 5/1965 | Strand | F16K 7/06 | 251/7 |
| 3,326,217 A * | 6/1967 | Kerr | A61B 17/1227 | 24/513 |
| 3,417,752 A * | 12/1968 | Butler | A61B 17/2833 | 24/303 |
| 3,852,045 A * | 12/1974 | Wheeler | A61F 2/28 | 419/2 |
| 4,035,849 A * | 7/1977 | Angell | A61F 2/2409 | 264/222 |
| 4,106,508 A * | 8/1978 | Berlin | A61B 17/1227 | 251/7 |
| 4,112,951 A * | 9/1978 | Hulka | A61B 17/282 | 128/831 |
| 4,281,646 A * | 8/1981 | Kinoshita | A61B 1/00068 | 134/104.1 |
| 4,449,532 A * | 5/1984 | Storz | A61B 1/00154 | 600/114 |
| 4,830,003 A * | 5/1989 | Wolff | A61F 2/86 | 606/191 |
| 4,867,139 A * | 9/1989 | Girzadas | A61B 17/02 | 600/210 |
| 4,895,573 A * | 1/1990 | Koeneman | A61F 2/30965 | 606/89 |
| 4,905,679 A * | 3/1990 | Morgan | A61B 17/8085 | 227/156 |
| 5,052,374 A * | 10/1991 | Alvarez-Jacinto | A61B 17/0293 | 600/218 |
| 5,297,538 A * | 3/1994 | Daniel | A61B 17/0206 | 600/206 |
| 5,312,426 A * | 5/1994 | Segawa | A61B 17/1227 | 24/545 |
| 5,313,934 A * | 5/1994 | Wiita | A61B 1/00091 | 600/109 |
| 5,351,675 A * | 10/1994 | Brodsky | A61B 1/127 | 126/263.08 |
| 5,392,766 A * | 2/1995 | Masterson | A61B 1/0008 | 15/244.1 |
| 5,400,767 A * | 3/1995 | Murdoch | A61B 1/00135 | 600/157 |
| 5,407,423 A * | 4/1995 | Yoon | A61B 17/0057 | 15/244.1 |
| 5,474,057 A * | 12/1995 | Makower | A61B 17/0218 | 600/205 |
| 5,549,543 A * | 8/1996 | Kim | A61B 1/3132 | 219/429 |
| 5,569,274 A * | 10/1996 | Rapacki | A61B 17/00234 | 128/898 |
| 5,683,349 A * | 11/1997 | Makower et al. | | 600/214 |
| 5,683,405 A * | 11/1997 | Yacoubian | A61B 17/1227 | 24/545 |
| 5,899,853 A * | 5/1999 | Fowler, Jr. | A61B 17/02 | 600/217 |
| 5,910,106 A * | 6/1999 | Morgan | F28D 20/028 | 126/263.05 |
| 5,944,657 A * | 8/1999 | Djurovic | A61B 17/0218 | 600/201 |
| 6,206,827 B1 * | 3/2001 | Chin | A61B 17/02 | 600/217 |
| 6,354,992 B1 * | 3/2002 | Kato | A61B 1/121 | 600/157 |
| 6,358,196 B1 * | 3/2002 | Rayman | A61B 17/00234 | 600/12 |
| 6,436,088 B2 * | 8/2002 | Frazier | A61B 1/121 | 604/500 |
| 6,494,211 B1 * | 12/2002 | Boyd | A61B 17/00234 | 128/898 |
| 6,607,475 B2 * | 8/2003 | Doyle | A61B 19/22 | 600/1 |
| 6,814,742 B2 * | 11/2004 | Kimura | A61B 17/083 | 606/142 |
| 7,311,660 B2 * | 12/2007 | Gomez | A61B 1/127 | 126/263.04 |
| 7,429,259 B2 * | 9/2008 | Cadeddu | A61B 17/0469 | 606/1 |
| 7,641,644 B2 * | 1/2010 | Chang | A61F 11/002 | 600/218 |
| 7,854,728 B2 * | 12/2010 | Boyle, Jr. | A61B 19/34 | 15/104.16 |
| 8,075,481 B2 * | 12/2011 | Park et al. | | 600/204 |
| 2002/0022762 A1 * | 2/2002 | Beane | A61B 1/122 | 600/101 |
| 2003/0009080 A1 * | 1/2003 | Peng | A61B 17/02 | 600/37 |
| 2003/0120132 A1 * | 6/2003 | Phillips | A61B 17/02 | 600/210 |
| 2004/0024291 A1 * | 2/2004 | Zinkel | A61B 17/0206 | 600/218 |
| 2005/0171493 A1 | 8/2005 | Nicholls | | |
| 2005/0251183 A1 | 11/2005 | Buckman et al. | | |
| 2005/0283137 A1 | 12/2005 | Doyle et al. | | |
| 2006/0149135 A1 | 7/2006 | Paz | | |
| 2007/0276412 A1 * | 11/2007 | Catanese | A61B 17/0401 | 606/143 |
| 2008/0058584 A1 * | 3/2008 | Hirotsuka | A61B 17/0401 | 600/37 |
| 2008/0064927 A1 * | 3/2008 | Larkin | A61B 1/00087 | 600/114 |
| 2008/0269779 A1 | 10/2008 | Caddedu | | |
| 2009/0209947 A1 | 8/2009 | Gordin et al. | | |
| 2009/0222029 A1 * | 9/2009 | Gordin | A61B 1/32 | 606/151 |
| 2009/0250081 A1 * | 10/2009 | Gordin et al. | | 134/6 |
| 2010/0174150 A1 * | 7/2010 | Park | A61B 17/0218 | 600/218 |
| 2012/0078057 A1 * | 3/2012 | Scott | A61B 17/0218 | 600/201 |

FOREIGN PATENT DOCUMENTS

| | | |
|---|---|---|
| WO | 2005/002415 A2 | 1/2005 |
| WO | 2008/041225 A2 | 4/2008 |
| WO | 2008/041226 A2 | 4/2008 |
| WO | 2008/041227 A2 | 4/2008 |

OTHER PUBLICATIONS

Response to Restriction Requirement filed Aug. 23, 2011 for Restriction Requirement mailed on Jul. 27, 2011 for U.S. Appl. No. 12/418,094, filed Apr. 3, 2009.
Restriction Requirement mailed Nov. 1, 2011 for U.S. Appl. No. 12/418,030, filed Apr. 3, 2009.
Office Action mailed Nov. 1, 2011 for U.S. Appl. No. 12/418,094, filed Apr. 3, 2009.
Response to Restriction Requirement mailed Nov. 1, 2011 for U.S. Appl. No. 12/418,030, filed Apr. 3, 2009 filed Dec. 1, 2011.
International Search Report mailed Jun. 18, 2008 for PCT/IL2007/001184 filed Sep. 25, 2007.
Written Opinion mailed Jun. 18, 2008 for PCT/IL2007/001184 filed Sep. 25, 2007.
International Search Report mailed Sep. 9, 2008 for PCT/IL2007/001185 filed Sep. 25, 2007.
Written Opinion mailed Sep. 9, 2008 for PCT/IL2007/001185 filed Sep. 25, 2007.
International Search Report mailed Mar. 10, 2009 for PCT/IL2007/001186 filed Sep. 25, 2007.
Written Opinion mailed Mar. 10, 2009 for PCT/IL2007/001186 filed Sep. 25, 2007.
International Preliminary Report on Patentability published Apr. 7, 2009 for PCT/IL2007/001184 filed Sep. 25, 2007.
International Preliminary Report on Patentability published published Apr. 7, 2009 for PCT/IL2007/001185 filed Sep. 25, 2007.

(56) References Cited

OTHER PUBLICATIONS

International Preliminary Report on Patentability published published Sep. 1, 2009 for PCT/IL2007/001186 filed Sep. 25, 2007.
International Preliminary Report on Patentability published Dec. 6, 2010 for PCT/IL2009/000550 filed Jun. 2, 2009.
U.S. Appl. No. 60/848,636, filed Oct. 3, 2006.
Response to Office Action for U.S. Appl. No. 12/418,094 submitted Mar. 25, 2012.
Office Action issued Jan. 26, 2012 for U.S. Appl. No. 12/418,030, filed Apr. 3, 2009.
Response to office action filed May 26, 2012 for U.S. Appl. No. 12/418,030.
Office Action for U.S. Appl. No. 12/418,128 dated Jun. 12, 2012.
International Search Report published Dec. 10, 2009 for PCT/IL2009/00550 filed Jun. 2, 2009.
Written Opinion of the International Searching Authority mailed Sep. 29, 2009 for PCT/IL2009/00550 filed Jun. 2, 2009.

\* cited by examiner

MULTI-COMPONENTS DEVICE, SYSTEM AND METHOD FOR ASSISTING MINIMALLY INVASIVE PROCEDURES

CROSS REFERENCE TO RELATED APPLICATIONS

The instant application is the U.S. national stage application of International Application No. PCT/IL2009/000550, filed on Jun. 2, 2009, which claims priority to U.S. provisional patent application 61/058,229, filed on Jun. 3, 2008, the entire disclosure of which is herein incorporated by reference.

FIELD OF THE INVENTION

The present invention generally relates to a multi components device, system and method for assisting minimally invasive surgical procedures. Including, but not limited to endoscopic surgery, key hole surgery, laparoscopic surgery, Single Port Access (SPA) and Natural Orifice Transluminal Endoscopic Surgery (NOTES).

BACKGROUND OF THE INVENTION

Endoscopic surgery interventions represent a significant advance in various fields of surgery that permit the performance of the majority of interventions through a number of small incisions that reduce postoperative pain and enhance postoperative recovery.

In endoscopic surgery, the surgeon performs the operation through small holes using large instruments and observing the internal anatomy with an endoscopic camera.

However, one of the main limitations of endoscopic surgical instruments is the need to go via a small hole or trocar, which limits the width of the instruments (for example, 5 mm width instruments for 5 mm diameter trocars, or 10 mm width instruments for 10 mm diameter trocars).

Therefore, there is a long felt need for a surgical instrument that while in a non-working state it can be introduced through a trocar (e.g., 5 mm trocars) and while in working configuration it can be significantly wider than the trocar that is used for the introduction or the removal of the instrument from the human cavity.

SUMMARY OF THE INVENTION

It is one object of the present invention to provide an elastic connector (ES) having at least two ends, each of which comprises attachment means for reversibly attaching said ES to at least two components; wherein said ES is characterized by a predetermined default configuration: and, a queue-like configuration in which said ES is adapted to provide simultaneous queue-like insertion or extraction of said at least two components through a tube or endoscope's working channel or a trocar into or from a body cavity; said ES is adapted to be reversibly transformed from said predetermined default configuration to said queue-like configuration and from said queue-like configuration to said predetermined default configuration.

It is another object of the present invention to provide the ES as defined above, wherein said default configuration is a parallel configuration in which said at least two components are positioned in a parallel manner one relative to another once said components are within said body cavity.

It is another object of the present invention to provide the ES as defined above, wherein said ES is adapted to articulate said at least two elements such that a joint is obtained between said two elements.

It is another object of the present invention to provide the ES as defined above, wherein said ES, when engaged with an introducer, is adapted to provide each of said components with at least four DOF within said body cavity; said four DOF are selected from translation and rotation.

It is another object of the present invention to provide the ES as defined above, wherein said four DOF are selected from DFx, DFy, DFz, DFroty or any combination thereof.

It is another object of the present invention to provide the ES as defined above, wherein said components are clips adapted to retract tissues, internal wall within said cavity or organs whining said body cavity by reversibly coupling to said tissues or said organs within said body cavity.

It is another object of the present invention to provide the ES as defined above, wherein said clip is characterized by a main longitudinal axis and having a distal, end and a proximal end coupled together by at least one shaft; said shaft is adapted to reciprocally move along said main longitudinal axis of said body; said shaft is at least partially encapsulated by at least one sleeve-like enveloping compression spring;

said proximal end comprising at least one actuation means coupled to the proximal end of said shaft;

said distal end comprising at least one movable jaw in mechanical communication with the distal end of said shaft, adapted to reversibly grasp at least one selected from a group consisting of internal surface within a body cavity, internal organ, tissue, blood vessel or any combination thereof; said movable jaw is characterized by at least one open configuration and at least one closed configuration; said movable jaw are adapted to be at least partially reversibly transformed from said open configuration to said closed configuration or from said close configuration to said open configuration;

said transformation is performed by reciprocally and linearly moving said actuation means along said longitudinal axis of said clip such that (i) said shaft is linearly moved towards and away said proximal end of said body; and, (ii) said compression spring is compressed or released such that said at least one movable jaw reconfigured.

It is another object of the present invention to provide the ES as defined above, wherein said is made of super elastic material.

It is another object of the present invention to provide the ES as defined above, wherein said ES is made of material selected from a group consisting of elastic materials, metals, stainless steel, plastics, silicon, rubber, metal, shape memory material, Nitinol, superelastic material or any combination thereof.

It is another object of the present invention to provide the ES as defined above, wherein said ES is characterized by (i) modulus young in the range of about 10 Pa to about 300 GPa; and, (ii) yield stress in the range of about 10 Pa to about 1 GPa.

It is another object of the present invention to provide the ES as defined above, wherein said attachment means is selected from a group consisting of any mechanical means, electrical mean, magnetic means or any combination thereof.

It is another object of the present invention to provide the ES as defined above, wherein said mechanical means are selected from a group consisting of vacuum, glue, undercut, snap attachment, pressure attachment, attachment by means of screws or latches or any combination thereof.

It is another object of the present invention to provide the ES as defined above, wherein said ES additionally comprises at least one cone shape centralization mechanism adapted to centralize said components so as to enable said simultaneous queue-like insertion into said tube or said endoscope's working channel or said trocar.

It is another object of the present invention to provide the ES as defined above, wherein said body cavity is selected from a group consisting of abdominal cavity and/or inside thoracic cavity and/or stomach cavity and/or into the pelvic cavity and/or inside a colon and/or heart during Minimally Invasive Surgery.

It is another object of the present invention to provide a retraction system used in minimal invasive surgeries, comprises
a. at least two clips;
b. at least one elastic connector (ES) having at least two ends, each of which comprises attachment means for reversibly attaching said ES to said at least two clips;
wherein said ES is characterized by a queue-like configuration in which said ES is adapted to provide simultaneous queue-like insertion or extraction of said at least two components through a tube or endoscope's working channel or a trocar into or from a body cavity; and, a predetermined default configuration; said ES is adapted to be reversibly transformed from said queue-like configuration to said predetermined default configuration and from said predetermined default configuration to said queue-like configuration.

It is another object of the present invention to provide the retraction system as defined above, wherein said default configuration is a parallel configuration in which said at least two components are positioned in a parallel manner one relative to another once said components are within said body cavity.

It is another object of the present invention to provide the retraction system as defined above, wherein said ES, when engaged with an introducer, is adapted to provide each of said clips with at least four DOF within said body cavity; said four DOF are selected from translation and rotation.

It is another object of the present invention to provide the retraction system as defined above, wherein said four DOF are selected from DFx, DFy, DFz, DFroty or any combination thereof.

It is another object of the present invention to provide the retraction system as defined above, wherein said clips are clips adapted to retract tissues, internal wall within said cavity or organs whining said body cavity by reversibly coupling to said tissues or said organs whining said body cavity.

It is another object of the present invention to provide the retraction system as defined above, wherein said clip is characterized by a main longitudinal axis and having a distal end and a proximal end coupled together by at least one shaft; said shaft is adapted to reciprocally move along said main longitudinal axis of said body; said shaft is at least partially encapsulated by at least one sleeve-like enveloping compression spring;
said proximal end comprising at least one actuation means coupled to the proximal end of said shaft;
said distal end comprising at least one movable jaw in mechanical communication with the distal end of said shaft, adapted to reversibly grasp at least one selected from a group consisting of internal surface within a body cavity, internal organ, tissue, blood vessel or any combination thereof; said movable jaw is characterized by at least one open configuration and at least one closed configuration; said movable jaw are adapted to be at least partially reversibly transformed from said open configuration to said closed configuration or from said close configuration to said open configuration;
said transformation is performed by reciprocally and linearly moving said actuation means along said longitudinal axis of said clip such that (i) said shaft is linearly moved towards and away said proximal end of said body; and, (ii) said compression spring is compressed or released such that said at least one movable jaw reconfigured.

It is another object of the present invention to provide the retraction system as defined above, wherein said connector is made of material selected from a group consisting of elastic materials, stainless steel, plastics, silicon, rubber, metal, shape memory material, Nitinol, superelastic material or any combination thereof.

It is another object of the present invention to provide the retraction system as defined above, wherein said ES is characterized by (i) modulus young in the range of about 10 Pa to about 300 GPa; and, (ii) yield stress in the range of about 10 Pa to about 1 GPa.

It is another object of the present invention to provide the retraction system as defined above, wherein said attachment means is selected from a group consisting of any mechanical means, electrical mean, magnetic means or any combination thereof.

It is another object of the present invention to provide the retraction system as defined above, wherein said mechanical means are selected from a group consisting of vacuum, glue, undercut, snap attachment, pressure attachment, attachment by means of screws or latches or any combination thereof.

It is another object of the present invention to provide the retraction system as defined above, wherein said ES additionally comprises at least one cone shape centralization mechanism adapted to centralize said clips so as to enable said simultaneous queue-like insertion into said tube or said endoscope's working channel or said trocar.

It is another object of the present invention to provide the retraction system as defined above, wherein said body cavity is selected from a group consisting of abdominal cavity and/or inside thoracic cavity and/or stomach cavity and/or into the pelvic cavity and/or inside a colon and/or heart during Minimally Invasive Surgery.

It is another object of the present invention to provide the retraction system as defined above, wherein said ES is adapted to articulate said at least two elements such that a joint is obtained between said two elements.

It is another object of the present invention to provide a method for retracting a first tissue or organ relatively to a second tissue or organ within a body cavity. The method comprises steps selected from:
a. obtaining an elastic connector (ES) in a predetermined default configuration; said ES having at least two ends, each of which comprises attachment means; said ES is characterized by a queue-like configuration; and, said predetermined default configuration; said ES is adapted to be reversibly transformed from said queue-like configuration to said predetermined default configuration and from said predetermined default configuration to said queue-like configuration;
b. obtaining at least two clips;
c. reversibly attaching each of said attachment means of said ES to said at least two clips;
d. inserting said ES coupled to said two clips in a queue-like manner through a tube or a endoscope's working channel or a trocar and into a body cavity, thereby providing said ES coupled to said two clips in said default configuration within said cavity;

e. grabbing said first tissue or said organ via one of said clips;

f. grabbing said second tissue or said organ via the second clip; thereby retracting said first tissue or said organ relatively to said second tissue or said organ.

It is another object of the present invention to provide the method as defined above, wherein each of said clips which is characterized by a main longitudinal axis and having a distal end and a proximal end coupled together by at least one shaft; said shaft is adapted to reciprocally move along said main longitudinal axis of said body; said shaft is at least partially encapsulated by at least one sleeve-like enveloping compression spring;

said proximal end comprising at least one actuation means coupled to the proximal end of said shaft;

said distal end comprising at least one movable jaw in mechanical communication with the distal end of said shaft, adapted to reversibly grasp at least one selected from a group consisting of internal surface within a body cavity, internal organ, tissue, blood vessel or any combination thereof; said movable jaw is characterized by at least one open configuration and at least one closed configuration; said movable jaw are adapted to be at least partially reversibly transformed from said open configuration to said closed configuration or from said close configuration to said open configuration;

said transformation is performed by reciprocally and linearly moving said actuation means along said longitudinal axis of said clip such that (i) said shaft is linearly moved towards and away said proximal end of said body; and, (ii) said compression spring is compressed or released such that said at least one movable jaw reconfigured.

It is another object of the present invention to provide the method as defined above, additionally comprising step of engaging said ES with an introducer and providing each of said clips with at least four DOF selected from translation and rotation.

It is another object of the present invention to provide the method as defined above, additionally comprising step of selecting said four DOF from DFx, DFy, DFz, DFroty or any combination thereof.

It is another object of the present invention to provide the method as defined above, additionally comprising step of providing said connector from material selected from a group consisting of elastic materials, stainless steel, plastics, silicon, rubber, metal, shape memory material, Nitinol, superelastic material or any combination thereof.

It is another object of the present invention to provide the method as defined above, additionally comprising step of selecting said attachment means from a group consisting of any mechanical means, electrical mean, magnetic means or any combination thereof.

It is another object of the present invention to provide the method as defined above, additionally comprising step of selecting said mechanical means from a group consisting of vacuum, glue, undercut, snap attachment, pressure attachment, attachment by means of screws or latches or any combination thereof.

It is still an object of the present invention to provide the method as defined above, additionally comprising step of providing said ES with at least one cone shape centralization mechanism adapted to centralize said clips so as to enable said simultaneous queue-like insertion into said tube or said endoscope's working channel or said trocar.

It is lastly an object of the present invention to provide the method as defined above, additionally comprising step of selecting said body cavity from a group consisting of abdominal cavity and/or inside thoracic cavity and/or stomach cavity and/or into the pelvic cavity and/or inside a colon and/or heart during Minimally Invasive Surgery.

BRIEF DESCRIPTION OF THE FIGURES

In order to understand the invention and to see how it may be implemented in practice, and by way of non-limiting example only, refer to the accompanying drawing.

DETAILED DESCRIPTION OF THE INVENTION

Figure 1:
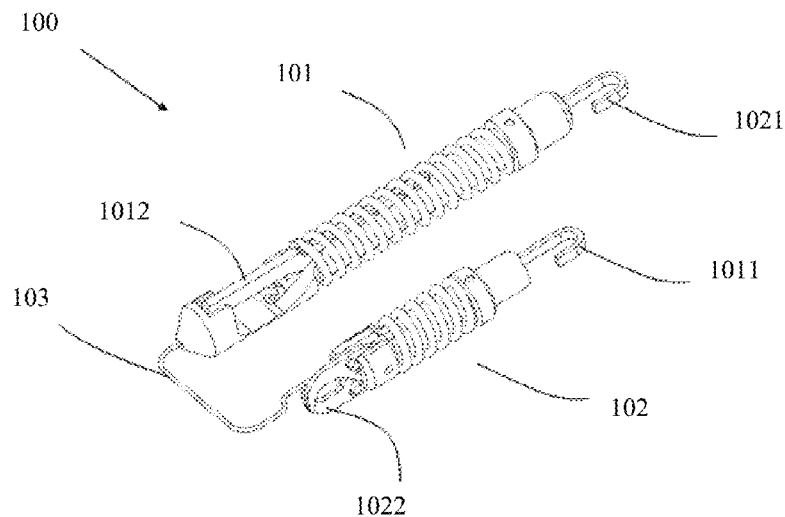
FIGS. 1 and 2A illustrate a perspective view of a two clip device connected with the elastic connector (ES), according to the present invention.

The following description is provided, as all chapters of the present invention, to enable any person skilled in the art of surgery to make use of the present invention and to implement the best modes contemplated by the inventor to carry it out. However, various modifications will be necessary, because the generic principles of the present invention are specific: to provide a surgical instrument compromising at least two connected components that might be introduced into the human cavity in single introduction to assist laparoscopic procedures. That is, it will be necessary to adapt the devices to future surgical activity.

U.S. application Ser. No. 10/563,229, PCT publication no. WO2005/002415, EP Application no. 04744933.5, U.S. Application No. 60/848,636, PCT publication no. IL2007/001185 and PCT publication no. IL2007/001186; are incorporated in all its parts as a reference to the current invention.

Exemplary descriptions and embodiments of the clip or the interchangeable tips may be found in U.S. application Ser. No. 10/563,229, PCT publication no. WO2005/002415, and EP Application no. 04744933.5.

The present invention presents a device which may be used during an endoscopic surgical procedure. The device consists of at least two components (namely clips) which are connected in such a way that they could be introduced into the abdomen cavity (or other openings e.g.; into a hollow body organs, and/or into natural/artificial orifices, and/or into spaces, and/or into post operative spaces), via a small hole or trocar in series (one component after the other).

Thus, in its working state inside the human cavity, the device can be larger than the trocar through which it was introduced.

The present invention also provides a system for the surgical procedure itself. The system comprises: (a) at least one device as the one mentioned above; and (b) at least one introducer.

The present invention also provides a method for retracting an internal organ during a surgical procedure. The method comprises steps selected inter alia from:
(a) Obtaining the above described system.
(b) Introducing the device into the abdomen cavity and/or into a hollow body organs and/or natural/artificial orifices and/or spaces and/or post operative spaces.
(c) Opening one jaw of the first clip via the introducer.
(d) Grabbing an internal organ or a tissue with the jaws of the first clip.
(e) Disconnecting the introducer from first clip and connecting the introducer to the second clip.
(f) Opening the jaws of the second clip with the introducer;
(g) Grabbing the internal wall of the abdominal cavity and/or a hollow body organ and/or natural/artificial orifices and/or spaces and/or post operative spaces with the jaws of the second clip.
(h) Disconnecting the introducer from the second clip.
(i) Removing the introducer from the abdominal cavity (and/or hollow body organs and/or natural/artificial orifices and/or spaces and/or post operative spaces). Thereby, additional incisions on the abdominal wall are not necessary.

The term "nitinol"" refers hereinafter to shape memory alloy—Nickel Titanium.

The term "superelastic material" refers hereinafter to any material that under high stress its deformation (strain) is 100% reversible.

The term "body cavity" refers hereinafter to the abdomen cavity or other openings e.g.; into a hollow body organs, and/or into natural/artificial orifices, and/or into spaces, and/or into post operative spaces.

The term "DOF" refers hereinafter to degrees of freedom which are a set of independent displacements and/or rotations that specify completely the displaced or deformed position and orientation of the system.

Figure 13:
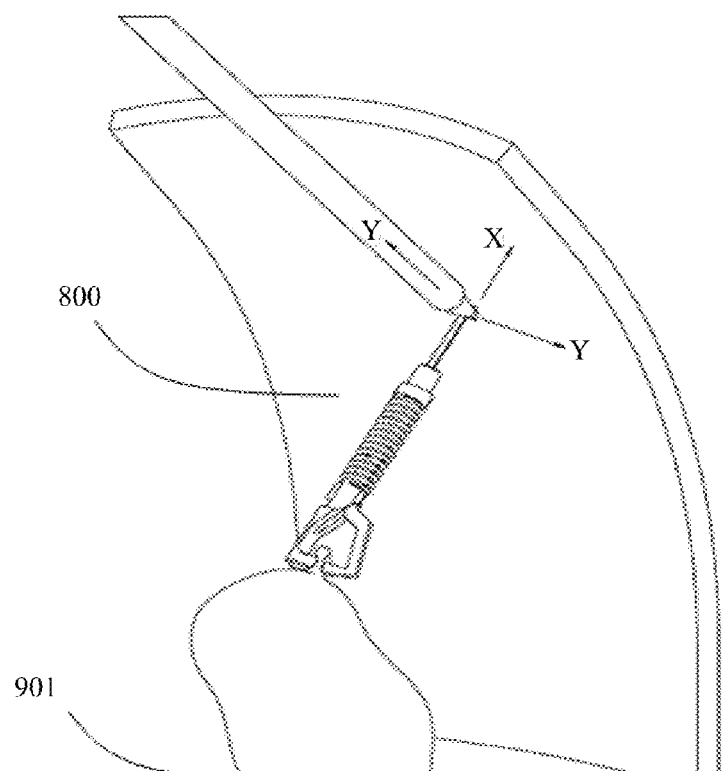
FIGS. 13-14 illustrate a retraction operation via using a single clip.

The term "DFx" refers hereinafter to linear movement along the X axis (as can be seen in FIG. 13).

The term "DFy" refers hereinafter to linear movement along the Y axis (as can be seen in FIG. 13).

The term "DFz" refers hereinafter to linear movement along the Z axis (as can be seen in FIG. 13).

The term "DFrotx" refers hereinafter to rotational movement around the X axis (as can be seen in FIG. 13).

The term "DFroty" refers hereinafter to rotational movement around the Y axis (as can be seen in FIG. 13).

The term "DFrotz" refers hereinafter to rotational movement around the Z axis (as can be seen in FIG. 13).

The term "parallel positioning" refers hereinafter to the position of the two components within a body cavity. Once to two components are inserted into the cavity—they are positioned in parallel manner one relative to the other (see FIG. 1).

The term "queue-like positioning" refers hereinafter to manner in which the two components are inserted into a body cavity through a trocar—see FIG. 8. In said queue-like positioning, the two elements are positioned in a queue-like manner.

The term "introducer" or "Applier" refers hereinafter to any surgical instrument specially designed for providing access during a surgery or operation.

The term "endoscopic surgery" refers hereinafter to procedures performed inside the body through small incisions, or within the lumen of an organ with the aid of a special camera.

The term "endoscopic instruments" refers hereinafter to surgical instruments or devices that are being used during endoscopic surgery.

The term "minimally invasive surgery" refers hereinafter to a procedure that includes penetrating the body through the skin, or through a body cavity or anatomical opening, with the smallest possible damage.

The term "shape memory materials" or "shape memory alloys" refers hereinafter to materials which are capable of "remembering" their original geometry. After a sample of shape memory materials is has been deformed from its original geometry, it regains its original geometry by itself during heating (one-way effect), or at higher ambient temperatures during unloading (pseudo-elasticity or super-elasticity). The thermally induced shape-memory effect has been described for different material classes: polymers, such as polyurethanes, poly(styrene-block-butadiene), polydioxanone and polynorbornene, metallic alloys, such as copper-zinc-aluminum-nickel, copper-aluminum-nickel, and nickel-titanium alloys.

The term "trocar" refers hereinafter to a surgical instrument that is used to introduce and to allow easy exchange of endoscopic instruments during endoscopic surgery.

The term 'default configuration' refers hereinafter to a default positioning of the two components. In said default positioning the two components can be in any angle one relatively to the other. One example to the default configuration is the parallel configuration.

The term 'parallel configuration' refers hereinafter to one example of a default configuration of the device (ES) in which the two components 101 and 102 are in a parallel positioning (i.e., parallel one to another)—see FIG. 1.

The term 'queue-like configuration' refers hereinafter to a configuration of the device in which the device (ES) is adapted to provide simultaneous queue-like insertion or extraction of the two components through a trocar into or from a body cavity. In the queue-like configuration, the two components are in a queue-like positioning—see FIG. 8.

It should be pointed out that in the present invention the term trocar can be used to indicate any device that enables endoscopic instruments exchange during laparascopic surgeries (e.g., catheter or endoscope).

Reference is now made to FIG. 1 to present a schematic and generalized illustration of a device 100 which comprises two components (namely clips): 101 and 102 connected with the elastic connector (ES) 103.

The ES is characterized by a queue-like configuration in which the ES is adapted to provide simultaneous queue-like insertion or extraction of the at least two components (102, 101) through a trocar into or from a body cavity.

The ES is also characterized by a predetermined default configuration. The ES is adapted to be reversibly transformed from the queue-like configuration to the predetermined default configuration and from the predetermined default configuration to the queue-like configuration.

One example of the default configuration is the parallel configuration in which the two components are positioned in a parallel manner one relative to another once said components are within the body cavity.

Since the ES is re-configurable from the default (e.g. parallel) configuration to the queue-like configuration and vise versa, the material from which the ES is made form should have the following mechanical properties:

On the one hand it should be elastic so as the ro-configuration from the default (e.g., parallel) configuration to the queue-like configuration would be enabled; and, on the other hand its strength should be high enough to overcome external forces (such as the element's weight) so as to enable the ro-configuration from the queue-like configuration to the default (e.g., parallel) configuration.

The mechanical characteristic of the ES should be as follows:

On the one hand it should have modulus young (the elastic modulus) in the range of about 10 Pa to about 300 GPa.

On the other hand it should have yield stress in the range of about 10 Pa to about 1 GPa.

In FIG. 1, the device is in its predetermined default configuration. In FIG. 1, the default configuration predetermined is a parallel configuration in which the two components 101, 102 parallel manner one to another (the parallel configuration).

The device 100 is especially useful in retracting tissues, internal wall within a cavity or organs whining a body cavity by reversibly coupling the two components to two tissues or two organs whining the body cavity.

Once the device is inserted into a body cavity, it can be used as an anchoring device adapted to be fastened to the undersurface of the abdomen wall via one of the clips 101 or 102. Moreover, said device can be used as a retractor by anchoring the first clip to a first tissue and the second clip to a second tissue such that a retraction id obtained.

Each of the components (e.g., clips) 101 and 102 compromises an interface to an introducer 1011 and 1021 respectively for actuating the component 101 and 102. It should be pointed out that if the components are clips—thus actuating the components mean—opening and closing the jaws of said clips.

According to one embodiment of the present invention, the ES is made of material selected from a group consisting of elastic materials, stainless steel, plastics, silicon, rubber, metal, shape memory material, Nitinol, superelastic material or any combination thereof.

Figure 2A:
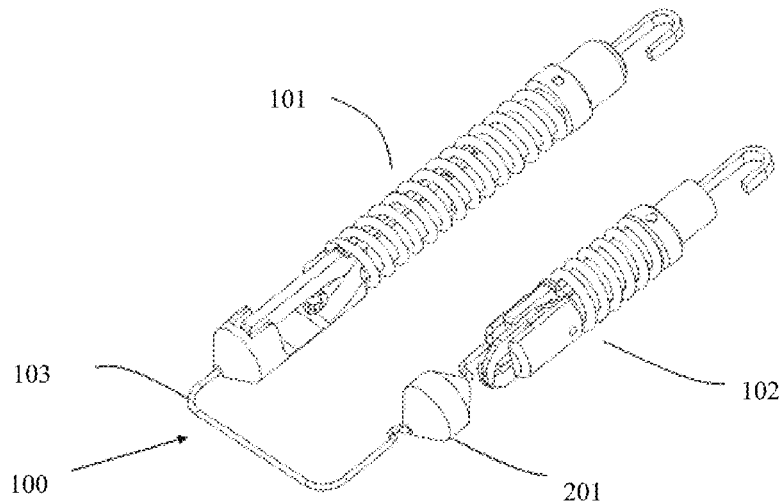

Reference is now made to FIG. 2a illustrating a schematic and generalized view of the device 100.

FIG. 2a also illustrates the elastic wire 103 which connects the two components 101 and 102.

The ES 100 comprises a double cone shape component 201 which functions as a concentric mechanism.

Once the first clip 101 is inserted into a tube (namely a trocar), clip 102 will be concentric to said tube.

It should be emphasized that the second clip will be centralized even if the connector 103 will be disrupted by some degree of plastic deformation.

Figure 2B:
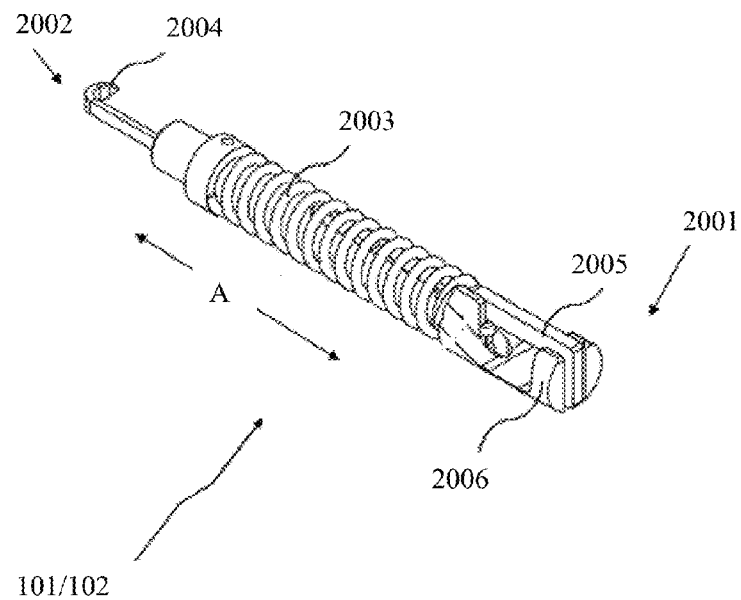
FIG. 2B is an example of a clip that can be used for the retraction.

According to one embodiment of the present invention the clip used for the retraction is as illustrated in FIG. 2b.

The clip 102/101 comprising a body, the body is characterized by a main longitudinal axis (illustrated in the figure as A) and having a distal end 2001 and a proximal end 2002 coupled together by at least one shaft (not shown).

The shaft is adapted to reciprocally move along said main longitudinal axis A of said body. The shaft is at least partially encapsulated by at least one sleeve-like enveloping compression spring (2003).

The proximal end 2002 comprising at least one actuation means (2004) coupled to the proximal end of said shaft for engaging with an introducer.

The distal end 2001 comprising at least one movable jaw (2005, 2006) in mechanical communication with the distal end of said shaft, adapted to reversibly grasp at least one selected from a group consisting of internal surface within a body cavity, internal organ, tissue, blood vessel or any combination thereof.

The movable jaw (2005, 2006) is characterized by at least one open configuration and at least one closed configuration. In the open configuration the two jaws are open and in the close configuration the two jaws are closed.

The movable jaw (2005, 2006) are adapted to be at least partially reversibly transformed from the open configuration to the closed configuration or from, the close configuration to the open configuration.

The transformation is performed by reciprocally and linearly moving the actuation means (2004) along the longitudinal axis (A) of the clip such that (i) the shaft is linearly moved towards and away said proximal end of said body; and, (ii) the compression spring (2003) is compressed or released such that said at least one movable jaw (2005, 2006) reconfigured.

In other words, the actuation means 2004 (activated by the introducer) retract and releases spring 2003. Once the spring is retracted the jaws 2005, 2006 are opened and may grab tissue or organ. Once the spring 2003 is released the jaws 2005, 2006 are in the closed configuration and can 'lock onto' the organ.

Figure 3:
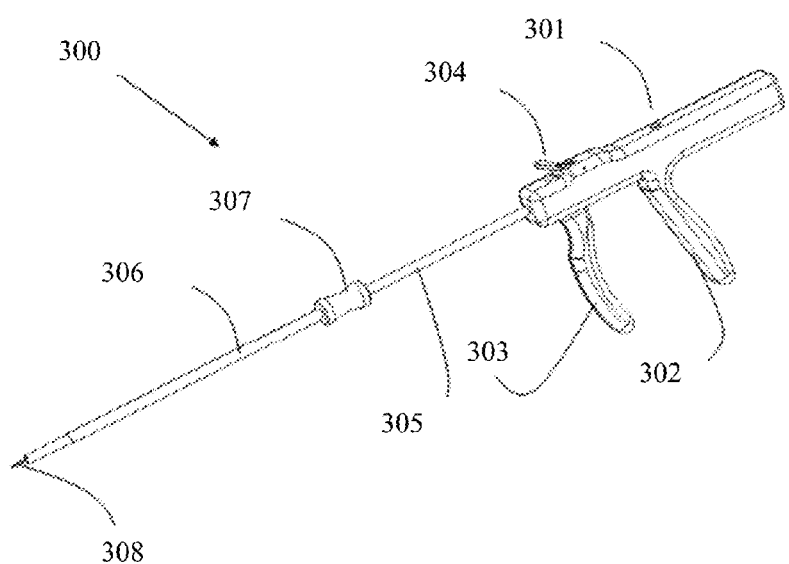
FIG. 3 is a perspective view of an introducer, which can be applied or introduced the device.

Reference is now made to FIG. 3 which schematically illustrates an introducer 300 to be used in conjugation with the above mentioned device.

The introducer comprises a body 301 having a handle 302, a trigger 303, a stopper 304, a tubular member 305 surrounded by a tubular sleeve 306 with a handle 307, and a distal engaging end 308.

Figure 4:
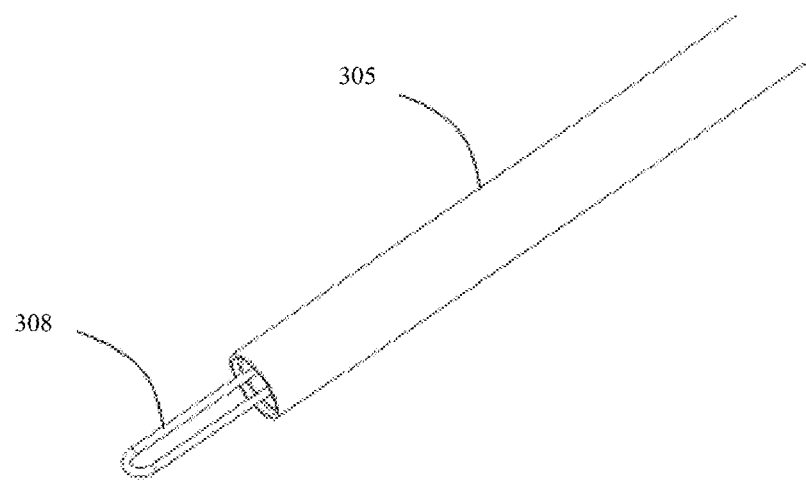
FIG. 4 is an enlarged sectional view of FIG. 3, focused on the interface to the device.

Reference is now made to FIG. 4 which schematically illustrates an enlarged sectional view of introducer 300. The scheme is focused on the edge of introducer 300, which compromises the distal engaging end 308.

Figure 5:
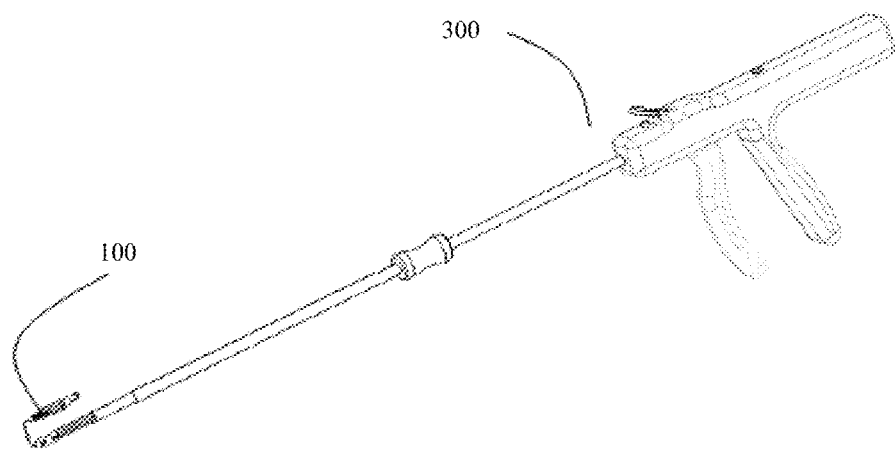
FIG. 5 illustrates the introducer 300 with device 100 connected to the distal engaging end 308.

Reference is now made to FIG. 5 which schematically illustrates the introducer 300 with device 100 connected to the distal engaging end 308.

Figure 6:
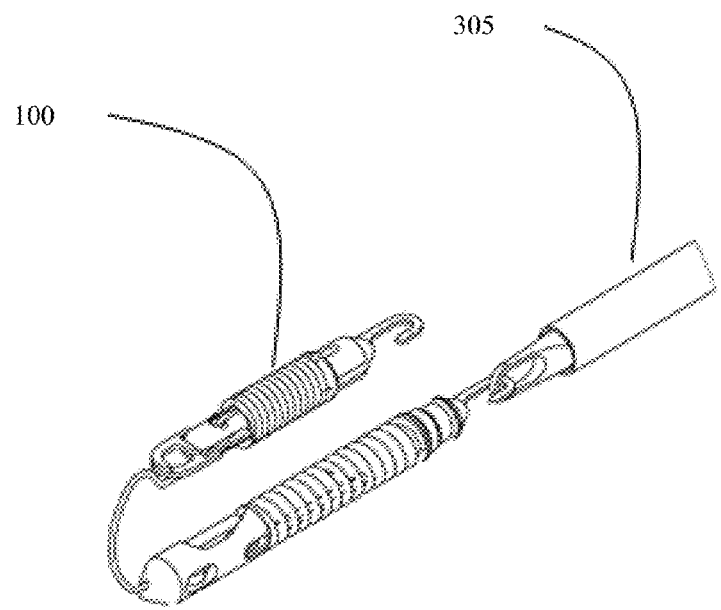
FIG. 6 provides a closer view of the distal engaging end 308.

Reference is now made to FIG. 6 which provide a closer view of the distal engaging end 308.

Figure 7:
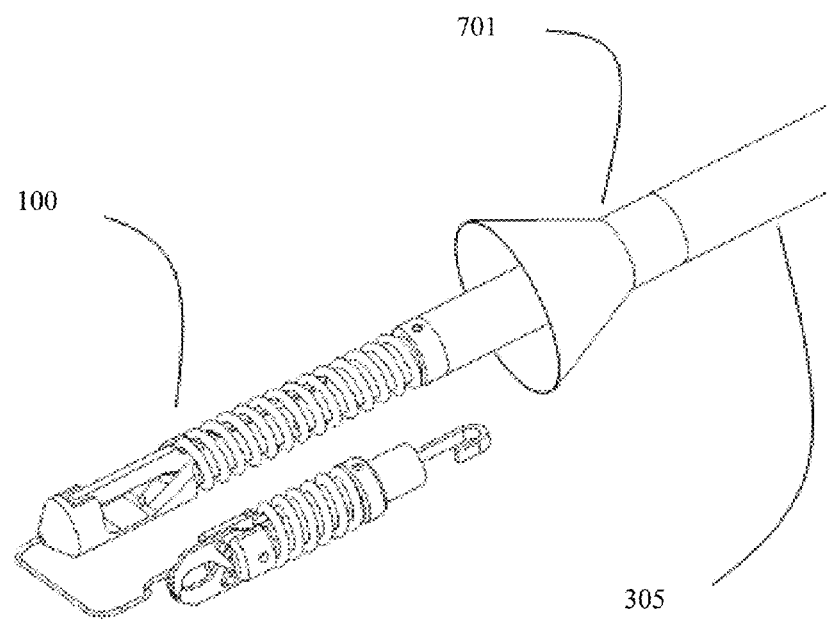
FIG. 7 schematically illustrates the edge of a similar introducer 300, only with an expanded cone shape element 701 that is attached to the introducer's sleeve 305.

Reference is now made to FIG. 7 which schematically illustrates the edge of a similar introducer 300, only with an expanded cone shape element 701 that is attached to the introducer's sleeve 305.

Such cone shape 701 element is adapted to bring the second component 102 of device 100 to be concentric to sleeve 305 when the device is pulled into it, so that device 100 will enter smoothly.

Figure 8:
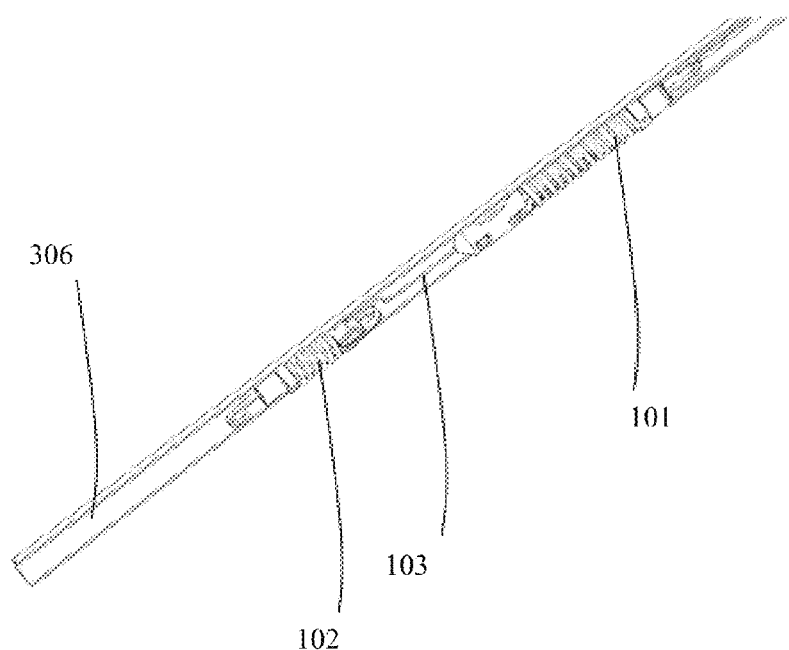
FIG. 8 illustrates a side cross section view of the introducer's sleeve 305 once device 100 is inserted into said sleeve 305.

Reference is now made to FIG. 8 which illustrates a side cross section view of the introducer's sleeve 305 once device 100 is inserted into said sleeve 305. The components 101, 102 are positioned in series (queue-like position) inside sleeve 305 (the queue-like configuration).

Such queue-like insertion is highly important since device 100 may be introduced into the human cavity or removed from the human cavity although its default width is larger than the sleeve's 305 diameter.

Reference is now made to FIGS. 9-12 which provide an example for the application of the device 100.

Once the device is inserted into a body cavity, the two clips (101 and 102) are positioned in a parallel manner.

Figure 9:
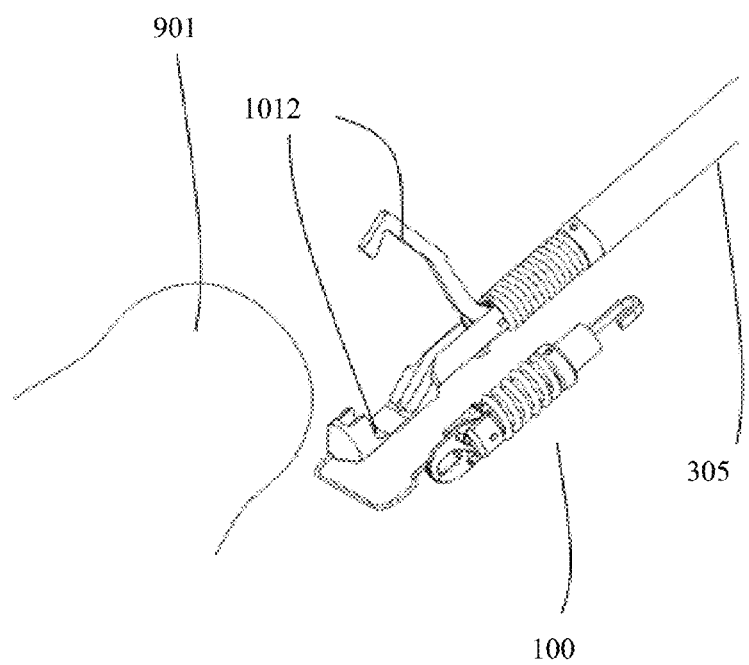
FIGS. 9-12 illustrate an example for the application of the device 100.
Figure 10A:
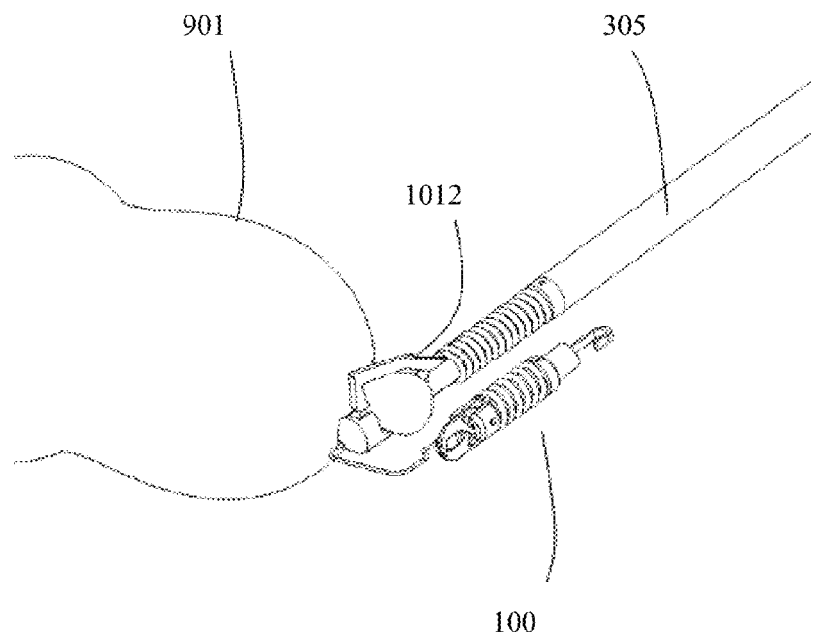

Next clip 101 is attached to an organ 901 (see FIGS. 9-10a). Such attachment is obtained by pulling the introducer trigger 303. Said trigger 303 activates the clip's jaws 1012—i.e., opens and close them; thus enabling the attachment between the clip's jaws 1012 and organ 901.

Afterwards, the introducer 300 is disengaged from clip 101 by pushing the introducer's stopper 304.

Figure 10B:
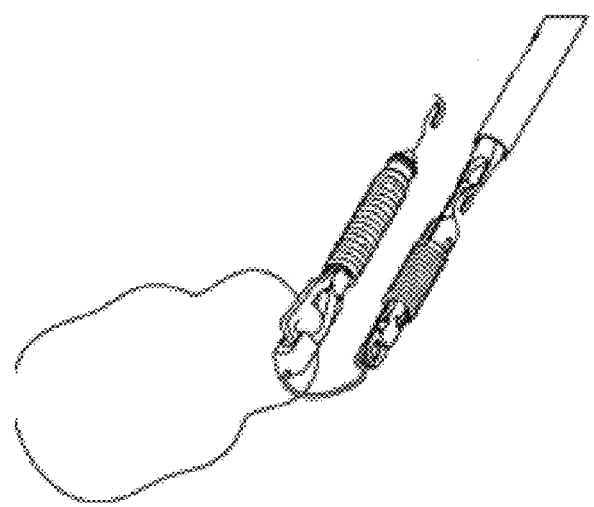

Next, said introducer 300 is engaged with clip 102 (see FIG. 10b).

Then, clip 102 is brought towards the desired location via introducer 300 within the internal cavity wall 1101.

Figure 11:
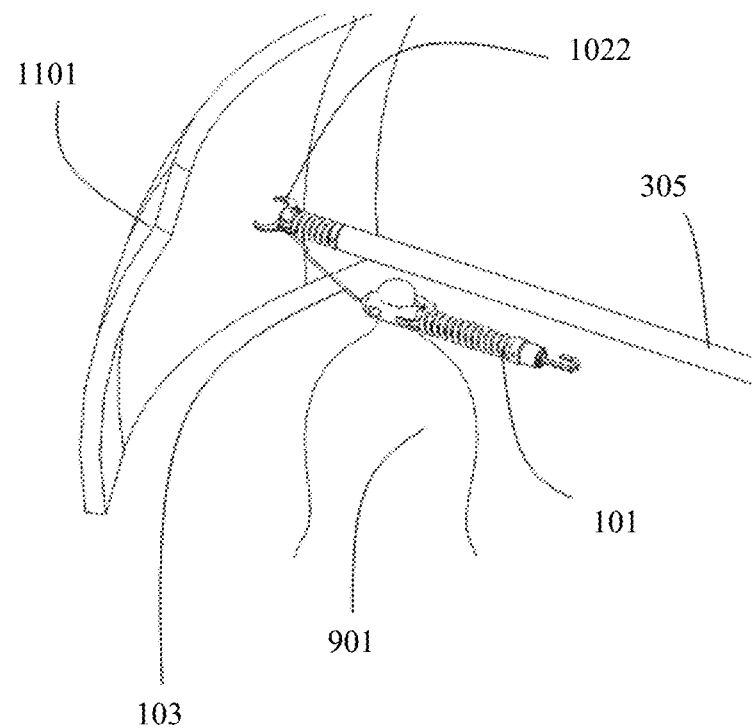
Figure 12:
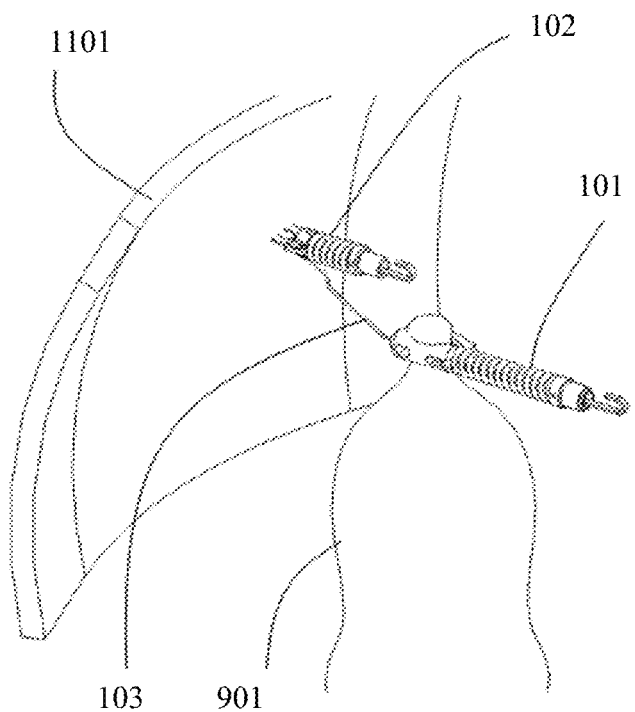

Next, in order to attach clip's 102 jaws the introducer's trigger 303 is pulled and the clip's jaws 1022 are opened; then by releasing the trigger 303, the jaws 1022 are closed on the internal cavity wall 1101 tissue (see FIGS. 11-12).

The last step is disengaging the introducer from clip 102 by pushing the introducer's stopper 304. Thereby the internal organ 901 is retracted as represented in FIG. 12.

Figure 14:
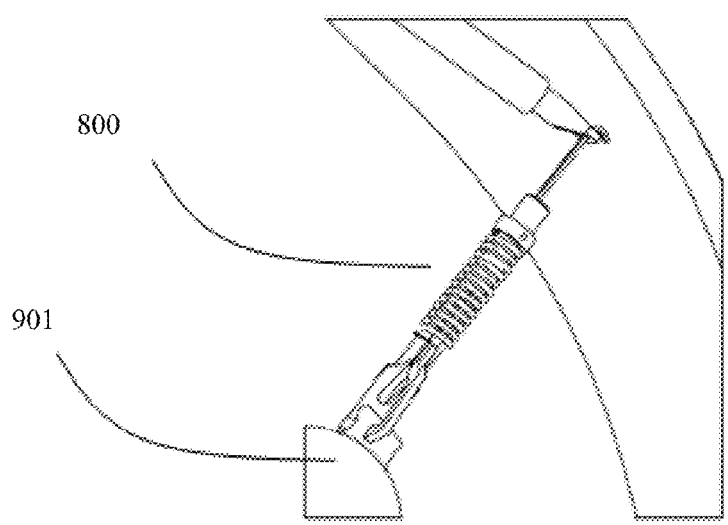

The following description is provided for better understanding the fundamental importance of the present invention as opposed to using a single clip:

Reference is now made to FIGS. 13 and 14 which illustrate a retraction operation via using a single clip.

In FIG. 13 a coordinate system (x-axis, y-axis and z-axis) is provided to better understand the significant improvement of the present invention.

As can be seen from FIGS. 13 and 14, in order to retract an organ 901 using a single clip 800, the surgeon has to first attach the clip to an organ and then to maneuver the clip attached to the organ to a second tissue or organ and hence to provide retraction.

Such a maneuvering is enabled in several degrees of freedom—along the x-axis, y-axis and a limited maneuver along the z-axis (the z-axis is limited due to the organ's limitation). However, since the attachment angle of the clip to the organ is the angle at which the clip will be attached to the tissue, the manipulation in order to obtain retraction is not simple and sometime impossible.

Figure 15:
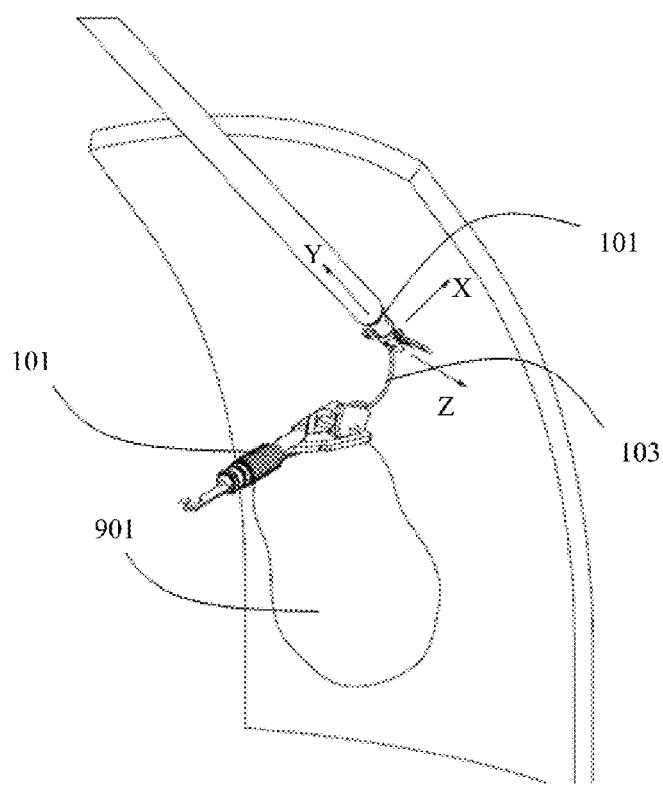
FIG. 15 illustrates again a retraction procedure using two clips device.

Reference is now made to FIG. 15 illustrating again a retraction procedure using two clips.

One of the major differences is the fact that the connector (i.e., the elastic connector (ES)) 103 performs as a joint such that the two clips are articulated connected. As a result of such a connection, the two clips are easily maneuvered one with respect to the other.

In other words, the two clips can be independently moved within the cavity.

As described above, this feature is further important since in the single clip configuration, the attachment angle of the clip to the organ is the angle at which the clip will be attached to the tissue. Usually said angle results in manipulation which is not simple and sometime impossible. As described above, by using the two clips device, the connector enables a relatively independent movement of one clip relatively to the other. Therefore, the angle at which the first clip was attached to the organ does not affect the angle at which the second clip is attached to the second tissue.

Yet another advantage of the two clips device is the increasing number of SOF. In the two clips device, the maneuvering of the second clip is enabled in an increased number of DOF—along the x-axis, y-axis, along the z-axis (it is emphasized that the maneuvering along the z-axis is not limited due to the connector 103), and around the y-axis.

Figure 16:
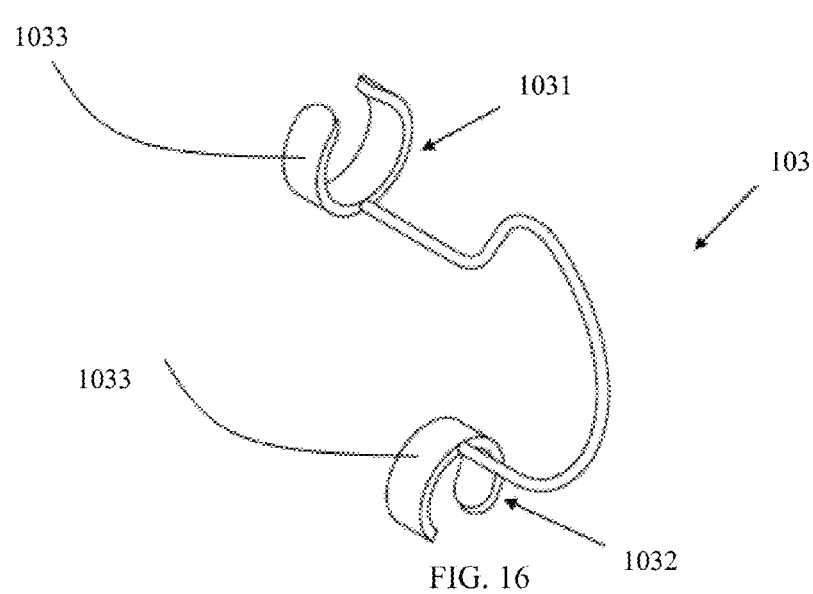
FIGS. 16-17 illustrate a closer view of the elastic connector (ES) connector 103.
Figure 17:
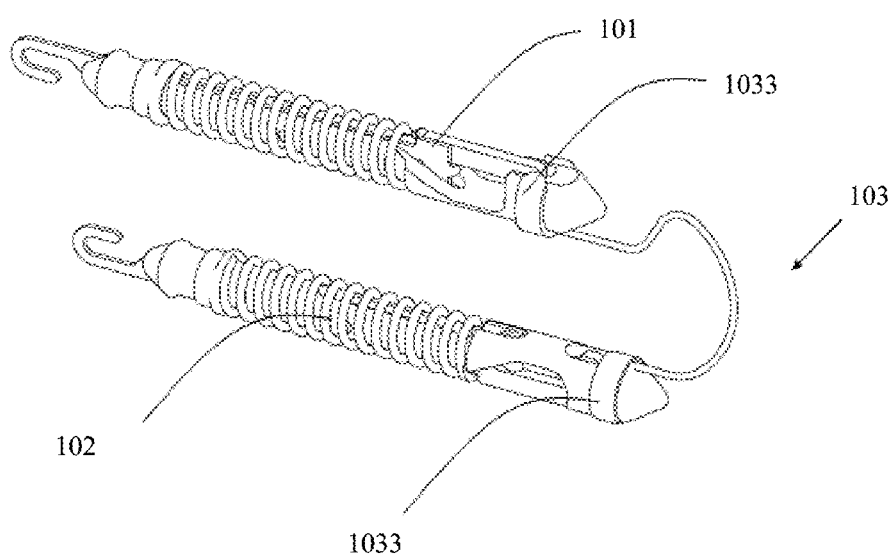

Reference is now made to FIGS. 16-17 providing a closer view of the elastic connector (ES) connector 103.

The connector comprises at least two ends 1031, 1032. Each of said ends comprises attachment means 1033 for reversibly attaching the ES to at least two components (namely clips 101 and 102, as can be seen in FIG. 17.

It should be pointed out that the attachment means 1033 can be any mechanical means (e.g., vacuum, glue, undercut, snap attachment, pressure attachment, attachment by means of screws or latches), electrical mean, magnetic means or any combination thereof.

It is emphasized that the ES is adapted to provide (i) simultaneous queue-like insertion of said at least two components through a trocar into a body cavity; and, (ii) a parallel positioning of said at least two components once said components are within said body cavity.

Figure 18:
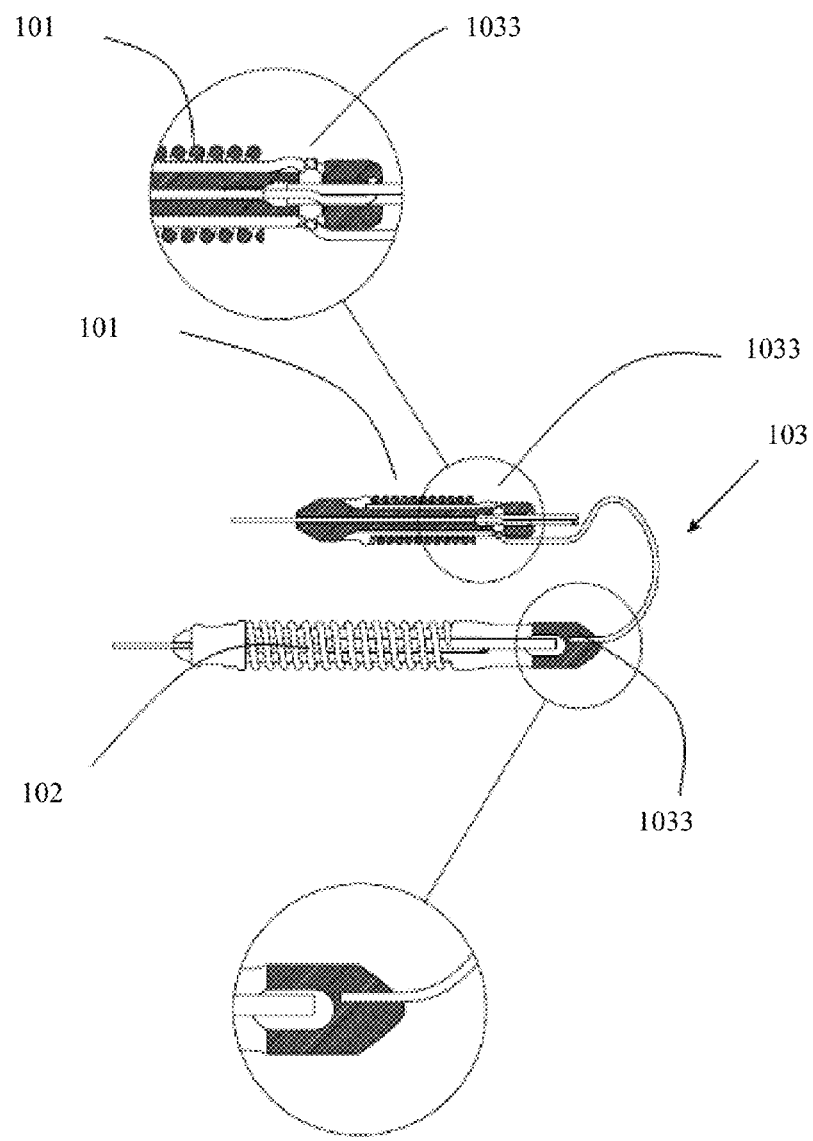
FIG. 18 illustrates a specific attachment between the attachment means 1033 of the connector 103 and the clips 101 and 102.

Reference is now made to FIGS. 17 and 18 illustrating a specific attachment between the attachment means 1033 of the connector 103 and the clips 101 and 102.

Said figures illustrates a mechanical attachment via pressure. Since the internal diameter of the attachment means 1033 is smaller than the external diameter of clips 101 and 102, in order to couple the connector 103 to clips 101 and 102, the attachment means 1033 are joined together via pressure.

After clips 101 and 102 are threaded into attachment means 1033 of the connector 103, 1033 applies pressures on clips 101 and 102 and creates friction between each clip and each attachment mean. Said pressure prevents the separation of each clip from the attachment means.

Figure 19:
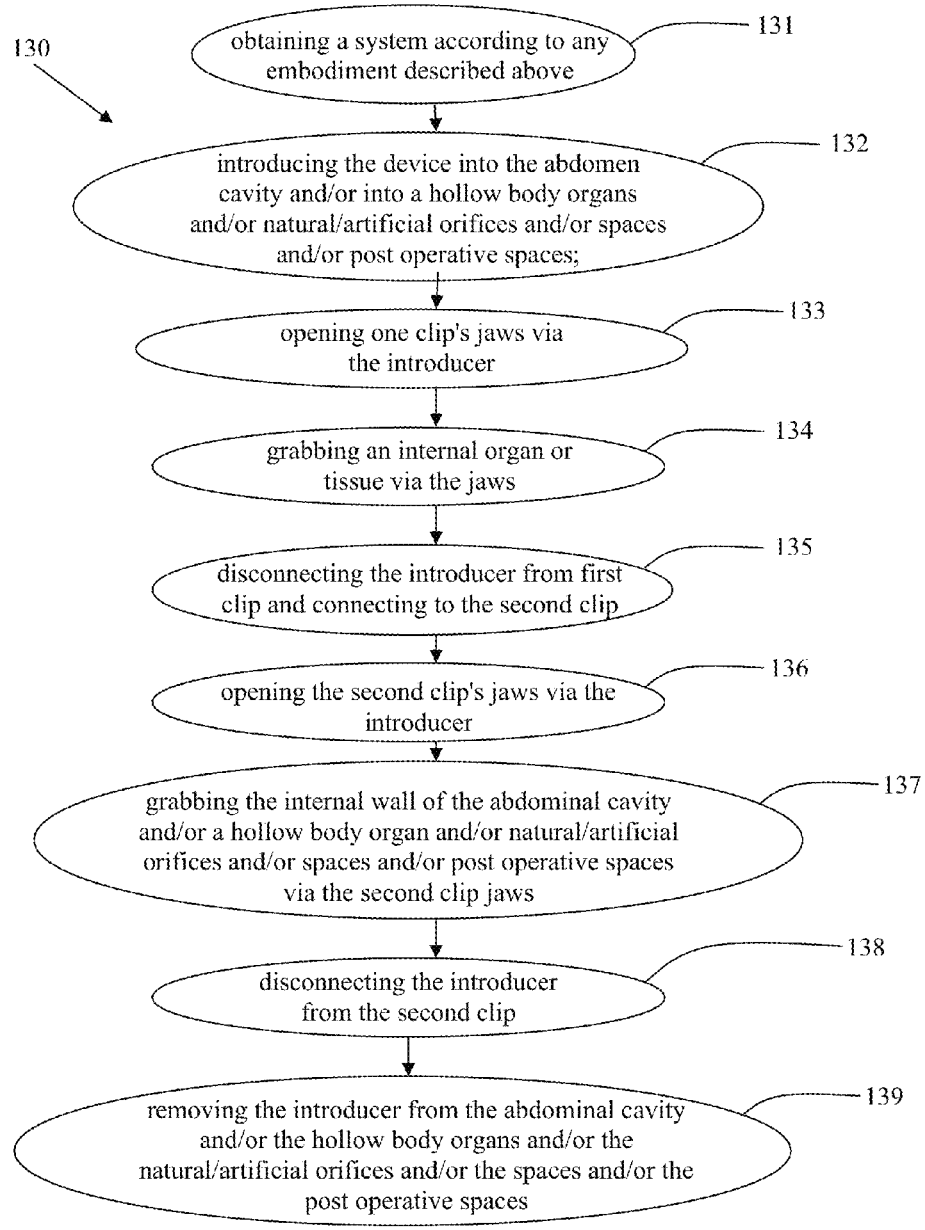
FIG. 19 schematically illustrates in a flow diagram a method of retracting an internal organ inside the human cavity.

Reference is now made to FIG. 19 representing a schematic flow diagram of the method (130) for retraction of an internal organ during a surgical procedure. First, (step 131) a device comprising the connector 103 and two clips 101 and 102 is obtained. The next stage is (132), the introduction of the device into a body cavity.

Then (step 133) one clip's jaws is opened via the introducer, and (step 134), an internal organ or tissue is grabbed via the jaws. Then (step 135), the introducer is disconnected from first clip, and connected to the second clip.

Then (step 136), the second clip's jaws is opened via the introducer, and (step 137) the second tissue or organ is grabbed via the jaws of the second clip.

Then (step 138) the introducer is disconnected from the second clip.

Finally, (step 139) the introducer is removed from the body cavity.

EXAMPLE

An example to a method for anchoring, without using additional significant incisions to the abdominal wall by using wired connected two clips:

In order to perform retraction of an internal organ during a minimally invasive procedure, without the need to add significant incisions to the abdominal wall or to use another trocar and a dedicated resource that should hold the organ during the retraction time, the use of an introducer and a device of the present invention may be applied. For instance:

Loading

1. Engage the interface 1011 of the clip 101 with the distal engaging end 308 of the introducer 300.
2. Pull the Introducer trigger 303 and release it. The stopper mechanism will lock trigger 303 in position, and the clip 101 will be loaded in the closed configuration (i.e., whilst its jaws are closed) at the end of the introducer tube 305. (As shown in FIGS. 5, 6).

3. Push the introducer sleeve 306 till it covers clip 101, the connector 103 and clip 102 (as shown in FIG. 8).

Insertion

4. Insert the loaded introducer into the abdomen through a trocar in position to the abdominal wall. Once the device 100 will be out of the introducer sleeve 306, it will change to default parallel like configuration due to the elastic characteristic of the flexible connector 103 (as shown in FIG. 6)
5. When the desired organ for retraction is reached, pull the trigger 303 to open clip's jaws 1012 (as shown in FIG. 9).

Retraction

6. Grab organ 901 in between clip's jaws 1012 and release the introducer's trigger 303 in order to close jaws 1012 on the organ (as shown in FIGS. 9-10).
7. Press once on stopper 304 in order to release clip 101 from the end of introducer 300.
8. Engage interface 1021 of clip 102 with the distal engaging end 308 of introducer 300.
9. Pull Introducer trigger 303 and release it. The stopper mechanism will lock trigger 303 in position, and clip 102 will be loaded in the closed configuration at the end of the introducer tube 305.
10. When the desired location on the internal wall inside the cavity is reached, pull trigger 303 to open clip's 102 jaws 1022 (as shown in FIG. 11).

Removal of the Introducer

11. Press once on stopper 304 in order to release clip 102 from the end of introducer 300.
12. Introducer 300 may now be removed through the trocar, leaving the device 100 in position.

Changing Retraction Position or Removing of the Device

13. Introduce empty introducer 300 through the trocar into the abdominal cavity.
14. Engage interface 1021 of the clip 102 with the distal engaging end 308 of introducer 200.
15. Pull trigger 303 to open clip's jaws 1022, and remove clip 102 from the internal cavity wall.
16. now there are the following options:
    a. Removal of the Device from the Human Cavity:
        1) Engage interface 1011 of clip 101 with the distal engaging end 308 of the introducer 300.
        2) Pull trigger 303 to open clip's 101 jaws 1012 and remove clip 101 from the internal retracted organ.
        3) Remove introducer 300 with device 100 from the human cavity through the trocar.
    b. Reposition of the Clip on the Abdominal Wall: Follow steps 8-10.
    c. Repetition of the Retraction Procedure on a Different Organ or at a Different Position: Follow steps 5-11.

The invention claimed is:

1. A retraction system comprising:
   an introducer comprising a tubular member and a distal engaging member disposed in said tubular member and operatively connected to a trigger;
   a plurality of clips having a stored orientation and a deployed orientation; and
   an elastic connector connected to said clips, wherein said elastic connector connects longitudinal ends of adjacent clips to each other;
   wherein in the stored orientation said clips are disposed in said tubular member and are positioned coaxially one after another along a longitudinal axis of said tubular member, each of said clips comprising grasping portions operative to grasp tissue, each of said grasping portions being engageable and movable by said distal engaging member upon suitable actuation of said trigger which causes engagement of said grasping portions with said distal engaging member and which moves said distal engaging member to actuate each of said grasping portions;
   and wherein in the deployed orientation said elastic connector is flexed about a flexure zone so that said clips are not coaxial with each other.

2. The retraction system according to claim 1, wherein the suitable actuation of said trigger causes sequential engagement of said grasping portions with said distal engaging member.

3. The retraction system according to claim 1, wherein in the deployed orientation said clips are parallel to each other.

4. The retraction system according to claim 1, wherein said elastic connector is adapted to provide the at least one of the clips to which it is attached with at least four degrees of freedom.

5. The retraction system according to claim 1, wherein said elastic connector is constructed of a shape memory material and flexes about the flexure zone due to shape memory properties of the material.

6. The retraction system according to claim 1, wherein said clips for retracting tissues, internal walls within said body cavity, or organs within a body.

7. The retraction system according to claim 1, wherein each of said clips comprises a hook element at one end thereof, and for each clip, said elastic connector is attached to said clip at an end opposite to said hook element.

8. A method for retracting body structure comprising using the retraction system of claim 1 to grasp and retract body structure with at least two of said clips.

* * * * *